United States Patent
Lewis et al.

(10) Patent No.: US 8,163,029 B2
(45) Date of Patent: Apr. 24, 2012

(54) EXTENDED RADIUS PROSTHESIS AND ASSOCIATED METHOD

(75) Inventors: Paul P. Lewis, Warsaw, IN (US); Barry A. Schnieders, Plymouth, IN (US)

(73) Assignee: Depuy Products, Inc.

( * ) Notice: Subject to any disclaimer, the term of this patent is extended or adjusted under 35 U.S.C. 154(b) by 965 days.

(21) Appl. No.: 10/881,205

(22) Filed: Jun. 30, 2004

(65) Prior Publication Data

US 2006/0004463 A1 Jan. 5, 2006

(51) Int. Cl.
*A61F 2/34* (2006.01)

(52) U.S. Cl. .................................... 623/22.38

(58) Field of Classification Search ............... 623/18.11, 623/22.11, 22.15, 22.17, 22.18, 22.19, 22.21, 623/22.24, 22.38

See application file for complete search history.

(56) References Cited

U.S. PATENT DOCUMENTS

| | | | |
|---|---|---|---|
| 4,457,306 A * | 7/1984 | Borzone | 606/1 |
| 4,704,127 A | 11/1987 | Averill et al. | |
| 4,892,549 A | 1/1990 | Figgie et al. | |
| 5,019,105 A * | 5/1991 | Wiley | 623/22.29 |
| 5,370,703 A | 12/1994 | Willert et al. | |
| 5,413,603 A | 5/1995 | Noiles et al. | |
| 5,443,519 A | 8/1995 | Averill et al. | |
| 5,549,698 A | 8/1996 | Averill et al. | |
| 5,571,201 A | 11/1996 | Averill et al. | |
| 5,609,646 A | 3/1997 | Field et al. | |
| 5,658,338 A | 8/1997 | Tullos et al. | |
| 5,676,704 A | 10/1997 | Ries et al. | |
| 5,702,477 A | 12/1997 | Capello et al. | |
| 5,725,487 A | 3/1998 | Freeman et al. | |
| 5,725,587 A | 3/1998 | Garber | |
| 5,824,108 A | 10/1998 | Huebner | |
| 5,858,020 A | 1/1999 | Johnson et al. | |
| 5,871,548 A | 2/1999 | Sanders et al. | |
| 5,879,405 A | 3/1999 | Ries et al. | |
| 5,928,288 A | 7/1999 | Wilson et al. | |
| 6,162,257 A | 12/2000 | Gustilo et al. | |
| 6,187,050 B1 | 2/2001 | Khalili et al. | |
| 6,322,564 B1 | 11/2001 | Surma | |
| 6,368,354 B2 | 4/2002 | Burstein et al. | |
| 6,402,787 B1 | 6/2002 | Pope et al. | |
| 6,416,553 B1 | 7/2002 | White et al. | |
| 6,451,058 B2 | 9/2002 | Tuke et al. | |
| 6,458,161 B1 | 10/2002 | Gibbs et al. | |
| 2002/0031675 A1 | 3/2002 | Cales et al. | |

(Continued)

FOREIGN PATENT DOCUMENTS

DE 33 10 944 A1 10/1984

(Continued)

OTHER PUBLICATIONS

European Search Report dated Oct. 18, 2005, for corresponding EP application 05253569.7.

(Continued)

*Primary Examiner* — Thomas J Sweet
*Assistant Examiner* — David Comstock

(57) ABSTRACT

An acetabular shell for use in a hip prosthesis is provided. The shell includes a body having an inner periphery and a convex outer periphery and defining a cavity of the body. The outer periphery has a first portion defining a hemisphere and a second portion extending from the equator of the first portion in a converging direction. The second portion forms a rim opposed to the equator. The cavity is positioned within the rim.

17 Claims, 19 Drawing Sheets

U.S. PATENT DOCUMENTS

2003/0171817  A1      9/2003  Rambert et al.

FOREIGN PATENT DOCUMENTS

| DE | 200 11 728 | U1 | 11/2000 |
|---|---|---|---|
| EP | 0 360 734 | A1 | 3/1990 |
| EP | 0 461 019 | A1 | 12/1991 |
| EP | 0846453 | A2 | 5/1997 |
| EP | 0 945 109 | A2 | 9/1999 |
| FR | 2 437 199 | A | 5/1980 |
| FR | 2 551 655 | A1 | 3/1985 |
| JP | 9-38120 | A | 7/1975 |
| WO | WO 98/22049 | A1 | 3/1998 |
| WO | WO 98/17206 | A1 | 4/1998 |
| WO | WO 02/00141 | A1 | 1/2002 |
| WO | WO 02/058597 | A2 | 8/2002 |

OTHER PUBLICATIONS

Japanese Search Report for Corresponding Patent Application No. 2005-190415, Dated Jan. 5, 2010, 4 Pages.

Australian Search Report for Corresponding Application No. 2005202696, Dated Apr. 7, 2010, 2 pages.

* cited by examiner

EXTENDED RADIUS PROSTHESIS AND ASSOCIATED METHOD

TECHNICAL FIELD OF THE INVENTION

The present invention relates generally to the field of orthopaedics, and more particularly, to an implant for use in arthroplasty.

BACKGROUND OF THE INVENTION

A joint within the human body forms a juncture between two or more bones or other skeletal parts. The ankle, hip, knee, shoulder, elbow and wrist are just a few examples of the multitude of joints found within the body. As should be apparent from the above list of examples of joints, many of the joints permit relative motion between the bones. For example, the motion of sliding, gliding, hinge or ball and socket movements may be had by a joint. For example, the ankle permits a hinge movement, the knee allows for a combination of gliding and hinge movements and the shoulder and hip permit movement through a ball and socket arrangement.

The joints in the body are stressed or can be damaged in a variety of ways. For example, the gradual wear and tear is imposed on the joints through the continuous use of a joint over the years. The joints that permit motion have cartilage positioned between the bones providing lubrication to the motion and also absorbing some of the forces direct to the joint. Over time, the normal use of a joint may wear down the cartilage and bring the moving bones in a direct contact with each other. In contrast, in normal use, a trauma to a joint, such as the delivery of a large force, from an accident for, example, an automobile accident, may cause considerable damage to the bones, the cartilage or to other connective tissue such as tendons or ligaments.

Arthropathy, a term referring to a disease of the joint, is another way in which a joint may become damaged. Perhaps the best known joint disease is arthritis, which is generally referred to a disease or inflammation of a joint that results in pain, swelling, stiffness, instability, and often deformity.

There are many different forms of arthritis, with osteoarthritis being the most common and resulting from the wear and tear of a cartilage within a joint. Another type of arthritis is osteonecrosis, which is caused by the death of a part of the bone due to loss of blood supply. Other types of arthritis are caused by trauma to the joint while others, such as rheumatoid arthritis, Lupus, and psoriatic arthritis destroy cartilage and are associated with the inflammation of the joint lining.

The hip joint is one of the joints that is commonly afflicted with arthropathy. The hip joint is a ball and socket joint that joins the femur or thighbone with the pelvis. The pelvis has a semispherical socket called the acetabulum for receiving a ball socket head in the femur. Both the head of the femur and the acetabulum are coated with cartilage for allowing the femur to move easily within the pelvis. Other joints commonly afflicted with arthropathy include the spine, knee, shoulder, carpals, metacarpals, and phalanges of the hand. Arthroplasty as opposed to arthropathy commonly refers to the making of an artificial joint. In severe cases of arthritis or other forms of arthropathy, such as when pain is overwhelming or when a joint has a limited range of mobility, a partial or total replacement of the joint within an artificial joint may be justified. The procedure for replacing the joint varies, of course, with the particular joint in question, but in general involves replacing a terminal portion of an afflicted bone with a prosthetic implant and inserting a member to serve as a substitute for the cartilage.

The prosthetic implant is formed of a rigid material that becomes bonded with the bone and provides strength and rigidity to the joint and the cartilage substitute members chosen to provide lubrication to the joint and to absorb some of the compressive forces. Suitable material for the implant include metals, and composite materials such as titanium, cobalt chromium, stainless steel, ceramic and suitable materials for cartilage substitutes include polyethylene. A cement may also be used to secure the prosthetic implant to the host bone.

A total hip replacement, for example, involves removing the ball shaped head of the femur and inserting a stem implant into the center of the bone, which is referred to as the medullary canal, or marrow of the bone. The stem implant may be cemented into the medullary canal or may have a porous coated surface for allowing the bone to heal directly to the implant. The stem implant has a neck and a ball shaped head, which are intended to perform the same functions as a healthy femur's neck and a ball shaped head. The polyethylene cup is inserted into the acetabulum and has a socket for receiving the head on the stem implant.

The polyethylene cup may be positioned directly into the acetabulum. Preferably, the polyethylene cup is secured to a metal member which is in turn secured to the acetabulum. This metal member is typically called a cup or a shell. The cup or shell may include a porous coating for promoting bony in-growth to secure the shell to the acetabulum. Alternatively or in addition the shell may include an opening or a plurality of openings for receiving bone screws to assist in the attachment of the shell to the acetabulum. As an alternative to the polyethylene cup, a cup of a different material may be inserted into the shell. For example, the cup may be made of a metal, for example, cobalt chromium, stainless steel, or titanium. Alternatively, the cup may be made of a ceramic.

For a variety of different reasons some surgeons want to position a shell with the face of the shell falling below the face of the acetabulum. Current attempts to accommodate a surgeon's desire to position the shell face below the face of the acetabulum include the use of a deep profile cup. A deep profile cup is a cup having a spherical portion and a cylindrical part extending from the spherical portion.

To accommodate the deep profile cup, bone must be removed or otherwise avoided when the cylinder is rotated about the shell outer periphery. Furthermore, when the bone is removed the press fit of the shell is reduced or gaps are generated between the shell or cup and bone. Such reduced pressed fit and gaps may reduce the long term fixation potential of the implant. Current deep profile shells include for example, SROM size DP+6 acetabular shells available from DePuy Orthopaedics, Inc., Warsaw, Ind. Such deep profile shells are used to increase shell anti-version. The increased shell anti-version is available since such shells they have an exterior profile that includes the full hemisphere and a cylinder. This shape gives more shell to bone interface with the host bone.

Referring now to FIG. 5, a prior art prosthesis in the form of a hip prosthesis is shown. The prosthesis 1 includes a hip cup or shell 2. The hip cup or shell 2 includes first hemispherical portion 3 from which extends a cylindrical portion 4. For proper fixation, the surgeon may prefer for all of the cylindrical portion 4 of the hip cup or shell 2 to extend below the acetabulum 5. If the orientation of the prosthesis 1 is required to be as shown as in FIG. 1, a portion, for example resected portion 6 of the acetabulum 5, must be removed.

Further, the positioning of the deep profile hip cup or shell 2 deep into the acetabulum 5 in order to obtain proper fixation of the shell or cup 2 to the acetabulum 5 may limit the range of motion for the prosthesis 1. First the cylindrical portion 4 of the hip shell or cup 2 and its mating cylindrical seat in the acetabulum inherently limit the angular position of the prosthesis 2. Further, when it is necessary to resect a portion of acetabulum, such a resection will be minimized and the impingement of the shell 2 will limit motion of the hip shell or the prosthesis 1 against the acetabulum 5.

Such a configuration is not optimal because the cylinder on top of the hemisphere prevents simple rotation of the shell and requires removal of the bone or reduces the amount of press fit at the shell or cup to bone interface.

SUMMARY OF THE INVENTION

According to the present invention, a modular implantable cup is provided. The cup or shell includes an outer profile that interfaces with bone and which is generally spherical in shape. Such a spherically shaped outer periphery of the cup or shell includes an outer periphery which is greater than a hemisphere or greater than 50% of the sphere. While the present invention may be well suited for use in a prosthetic hip implant for an acetabular cup, it should be appreciated that the invention should be applied to other joints as well. For example, the present invention can be utilized in a shoulder or other articulating joint.

According to one embodiment of the present invention, there is provided an acetabular shell for use in a hip prosthesis. The shell includes a body having an inner periphery and a convex outer periphery and defining a cavity of the body. The outer periphery has a first portion defining a hemisphere and a second portion extending from the equator of the first portion in a converging direction. The second portion forms a rim opposed to the equator. The cavity is positioned within the rim.

According to another embodiment of the present invention there is provided a hip cup for use in hip prosthesis. The cup includes a shell having a body having an inner periphery and a convex outer periphery and defining a cavity of the body. The outer periphery has a first portion defining a hemisphere and a second portion extending from the equator of the first portion in a converging direction. The second portion forms a rim opposed to the equator. The cavity is positioned within the rim. The cup also includes a liner to cooperate with the shell.

According to yet another embodiment of the present invention there is provided a hip prosthesis for use in hip arthroplasty. The prosthesis includes a stem for implantation into the medullary canal and a hip cup. The hip cup includes a liner and a shell. The shell has a body having an inner periphery and a convex outer periphery and defining a cavity of the body. The outer periphery has a first portion defining a hemisphere and a second portion extending from the equator of the first portion in a converging direction. The second portion forms a rim opposed to the equator. The cavity is positioned within the rim.

According to a further embodiment of the present invention, there is provided a method for providing hip arthroplasty. The method includes the steps of providing a hip prosthesis including a shell having an external spherical periphery extending beyond the equator of the spherical periphery, cutting an incision in the patient, preparing the acetabulum for receiving the shell, assembling the shell into the acetabulum, and orienting the shell relative to the acetabulum to optimize the hip prosthesis. The technical advantages of the present invention include the ability of the implant of the present invention to position the shell with the face of the shell not falling below the face of the acetabulum. The superior position of the shell relative to the acetabulum provides for improved range of motion for the patient. For example, according to one aspect of the present a shell is provided with a convex outer periphery and having a first portion defining a hemisphere, and a second portion extending from the equator. The second portion likewise has a convex outer periphery. Thus the present invention provides for a shell with a face not falling below the acetabulum.

The technical advantages of the present invention also include the ability of the implant of the present invention to avoid the removal of bone to rotate the cylindrical portion of shell around the face. For example, according to one aspect of the present invention a shell is provided with a generally spherical shape and a first portion defining a hemisphere and a second portion extending from the first portion. Thus the present invention provides for the rotation of the cylindrical portion of the shell around the face without the additional removal of bone.

The technical advantages of the present invention further include the ability to improve the contact between the shell and the acetabulum, and thereby improve long term fixation. For example, according to another aspect of the present invention a shell is provided with a generally spherical shape and includes a first portion defining a hemisphere and a second portion extending from the first portion. Thus the present invention provides for improved contact with the shell and the acetabulum, improving long term fixation.

Yet another technical advantage of the present invention is the ability of the present invention of the implant to permit simple rotation of the shell with a deep profile shell. For example, according to yet another aspect of the present invention an acetabular cup is provided with the outer periphery defined by a locus of points extending from an origin. Thus, the present invention provides for the simple rotation of a shell with a deep shell profile.

Yet another technical advantage of the present invention includes the ability to provide reduced press fit at the shell acetabulum interface for a deep profile shell. For example, according to yet another aspect of the present invention a shell is provided with a generally spherical shape including a first portion hemisphere and a second portion extending from the first portion defining a portion of a hemisphere. Thus the present invention provides for reduced press fit at the shell acetabulum interface with a deep profile shell.

The technical advantages of the present invention further include the ability the shell or cup to permit and maintain 180 degrees full hemispherical shell interface for an improved press fit. For example, according to one aspect of the present invention the acetabular shell has a spherical shape and includes a first portion defining a hemisphere and a second portion extending from the first portion. Thus the present invention provides for 180 degrees full hemispherical shell/bone interface even if the shell is rotated.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 16 is a flow chart of a method for performing arthroplasty in accordance with another embodiment of the present invention.

DETAILED DESCRIPTION OF THE INVENTION

Embodiments of the present invention and the advantages thereof are best understood by referring to the following descriptions and drawings, wherein like numerals are used for like and corresponding parts of the drawings.

Figure 5:
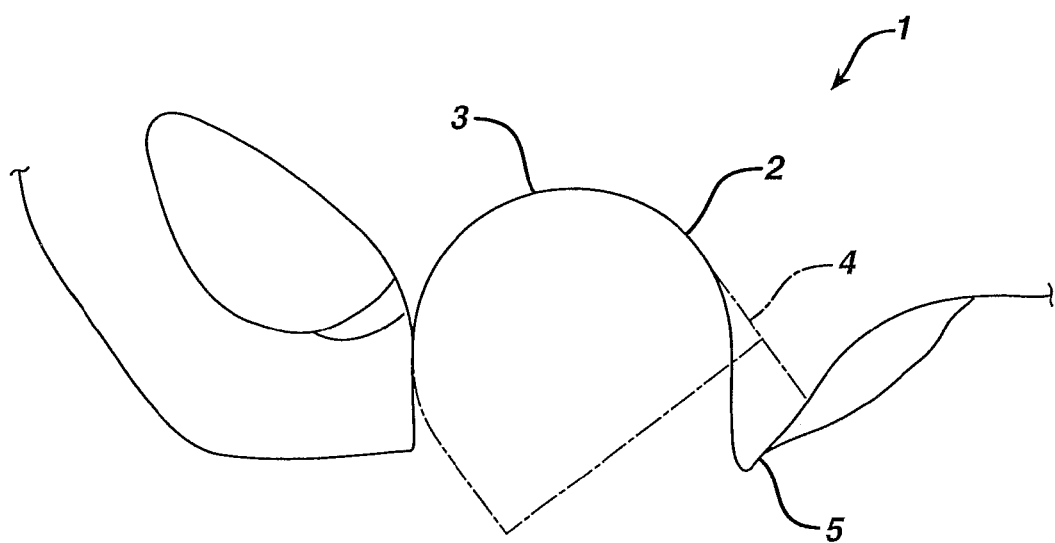
FIG. 5 is a plan view partially in cross section of a prior art hip cup shown in position in the acetabulum of a patient.

Referring now to FIG. 5, a prior art prosthesis in the form of a hip prosthesis is shown. The prosthesis 1 includes a hip cup or shell 2. The hip cup or shell 2 includes first hemispherical portion 3 from which extends a cylindrical portion 4. For proper fixation, the surgeon may prefer for all of the cylindrical portion 4 of the hip cup or shell 2 to extend below the acetabulum 5. If the orientation of the prosthesis 1 is required to be as shown as in FIG. 1, a portion, for example resected portion 6 of the acetabulum 5, must be removed.

Further, the positioning of the deep profile hip cup or shell 2 deep into the acetabulum 5 in order to obtain proper fixation of the shell or cup 2 to the acetabulum 5 may limit the range of motion for the prosthesis 1. First the cylindrical portion 4 of the hip shell or cup 2 and its mating cylindrical seat in the acetabulum inherently limits the angular position of the prosthesis 2. Further when it is necessary to resects portion of acetabulum, such a resection will be minimized and the impingement of the shell 2 with the limit motion of the hip shell or the prosthesis 1 against the acetabulum 5.

Figure 1:
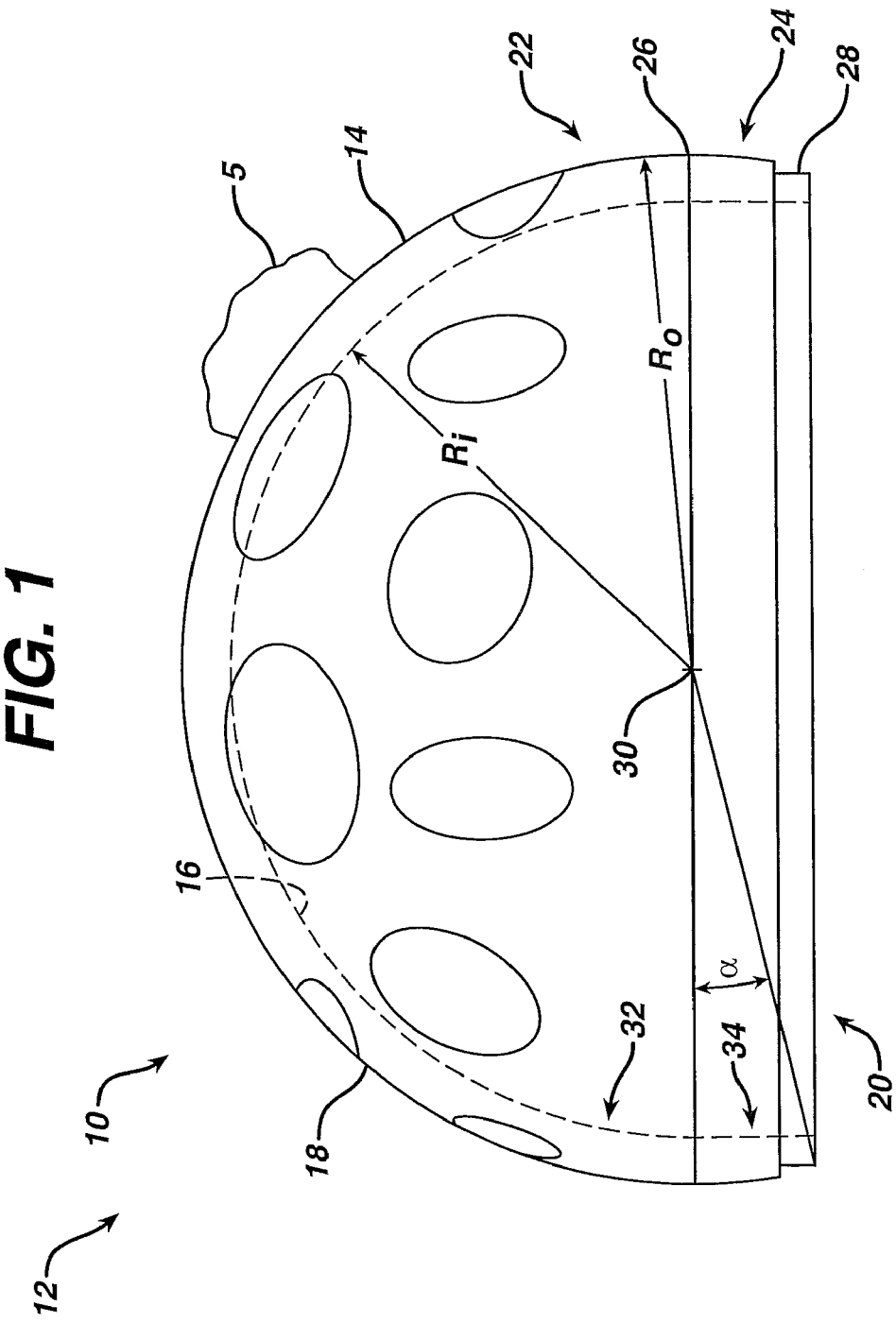
FIG. 1 is a plan view of an acetabular hip cup including the extended radius profile in accordance with the present invention.

According to the present invention and referring now to FIG. 1, an acetabular cup or shell is shown in use in a hip prosthesis 12. The shell 10 includes a body 14 having inner periphery 16 and a convex outer periphery 18. The body 14 defines a cavity 20 thereof. The outer periphery 18 includes a first portion 22 defining a hemisphere. The outer periphery further includes a second portion 24 extending from the equator 26 of the first portion 22 in a converging direction. The second portion 24 forms a rim 28 spaced from the equator. The cavity 20 is positioned within the rim 28.

As shown in FIG. 1, the inner periphery 16 may be concave. The inner periphery 16 if concave may be concentric with the convex outer periphery 18.

As shown FIG. 1, the first portion 22 of the convex outer periphery 18 of the body 14 may be defined by a locus of points extending a fixed distance from a origin 30. For example and is shown in FIG. 1, the first portion 22 of the convex outer periphery 18 may be defined by a locus of points extending a radius R from origin 30.

As shown in FIG. 1, the second portion 22 of the outer periphery 18 of the body 14 may similarly be defined by a locus of points extending at fixed distance from the origin 30. For example, and as is shown in FIG. 1, the second portion 24 may be defined by a radius R by extending from origin 30.

For simplicity and as is shown in FIG. 1, the rim 28 of the acetabular shell 10 may be spaced from and may be generally parallel to the equator 26.

As shown in FIG.1, the rim 28 and the equator 26 may, as shown, define an angle a extending from the origin 30. The angle α may be selected to position the acetabular cup deep enough into the acetabulum so that the rim 28 may be positioned below the surface of the acetabulum and so that the acetabular shell 10 may have suitable fixation to the acetabulum 5. For example, the angle α may be from 0 to 25 degrees. Preferably the angle α is from 0 to 10 degrees and may, for example, be from 0 to 5 degrees.

The inner periphery 16 may have any suitable shape. The inner periphery 16 may be adapted for receiving a head or ball of the hip prosthesis 12. Alternatively, the inner periphery 16 may be adapted for receiving a liner (not shown). The liner or may be adapted for receiving the ball or head.

As shown in FIG. 1, the inner periphery 16 may be concave. For example, the concave inner periphery 16 may be generally hemispherical. The concave inner periphery 16 may define first portion 32 of the inner periphery 16. The first portion 32 of the inner periphery 16 may be parallel and spaced from the first portion 22 of the outer periphery 18. The first portion 32 of the inner periphery 16 may be defined by a radius Ri extending from origin 30. The inner periphery 16 may further include a second portion 34 extending outwardly from the first portion 32 of the inner periphery 16. The second portion 34 may be generally cylindrical or may have any shape capable of receiving the liner or bearing or capable of receiving the head or ball.

Figure 2:
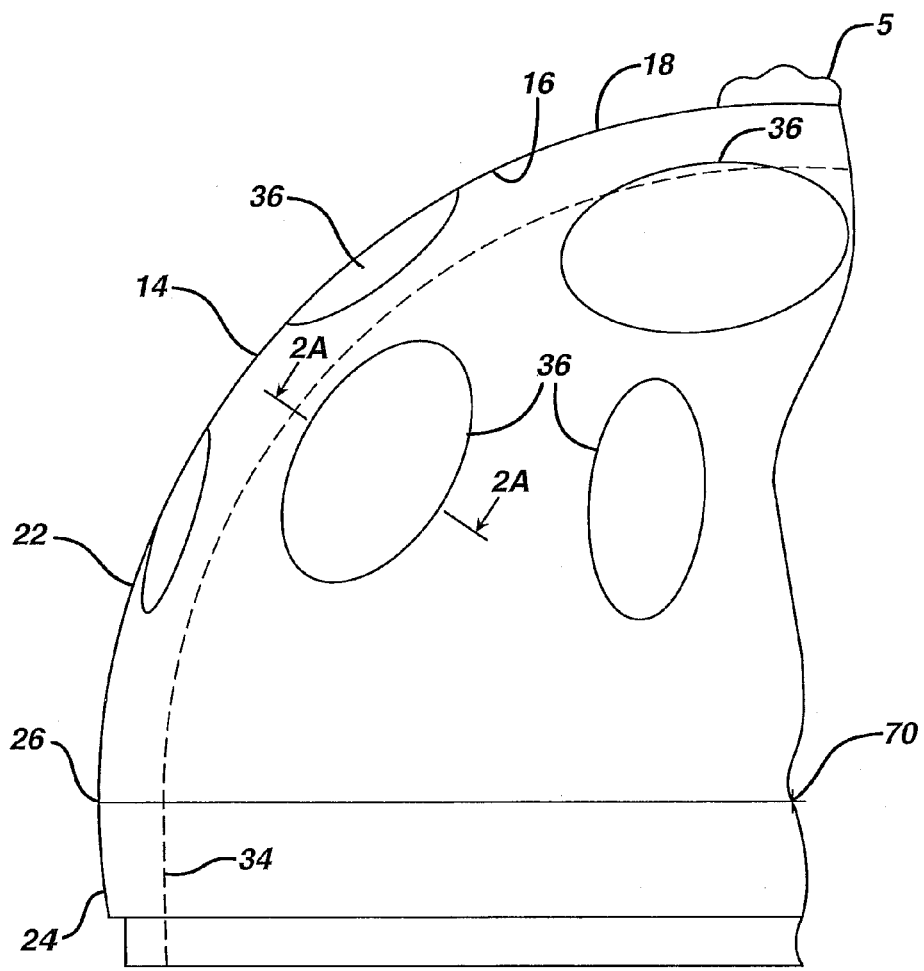
FIG. 2 is a partial plan view of FIG. 1.

Referring now to FIG. 2, the acetabular shell 10 of the hip prosthesis 12 is shown in greater detail. As shown in FIG. 2, the acetabular shell 10 of the hip prosthesis 12 may include a hole or aperture 36 passing through body 14. The hole or aperture 36 may be suitable for securing a fastener in the form of, for example, a bone screw (not shown). The holes 36 may extend from the outer periphery 18 through inner periphery 16. The hole 36 has shown in FIG. 2 may have be generally a cylindrical diameter D. While a solitary hole 36 may be sufficient for securing shell 10 to the acetabulum 5, it should be appreciated that a plurality of holes 36 as shown in FIG. 2, may be utilized. The holes 36 may be randomly distributed along the body 14 or may be positioned in a pattern or uniformly distributed.

Figure 2A:
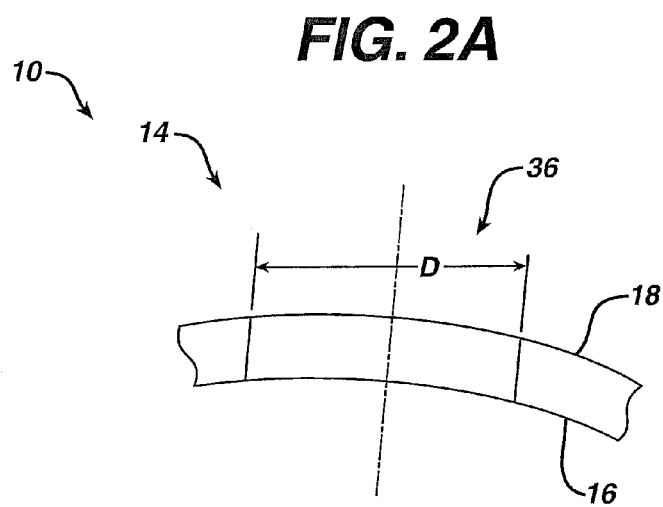
FIG. 2A is a partial plan view of FIG. 2, showing one of the holes in greater detail.

Referring now to FIG. 2A, a hole 36 is shown in cross section of the body 14 of the shell 10. The hole 36 may have a diameter D and extends from outer periphery 18 through inner periphery 16.

Figure 2B:
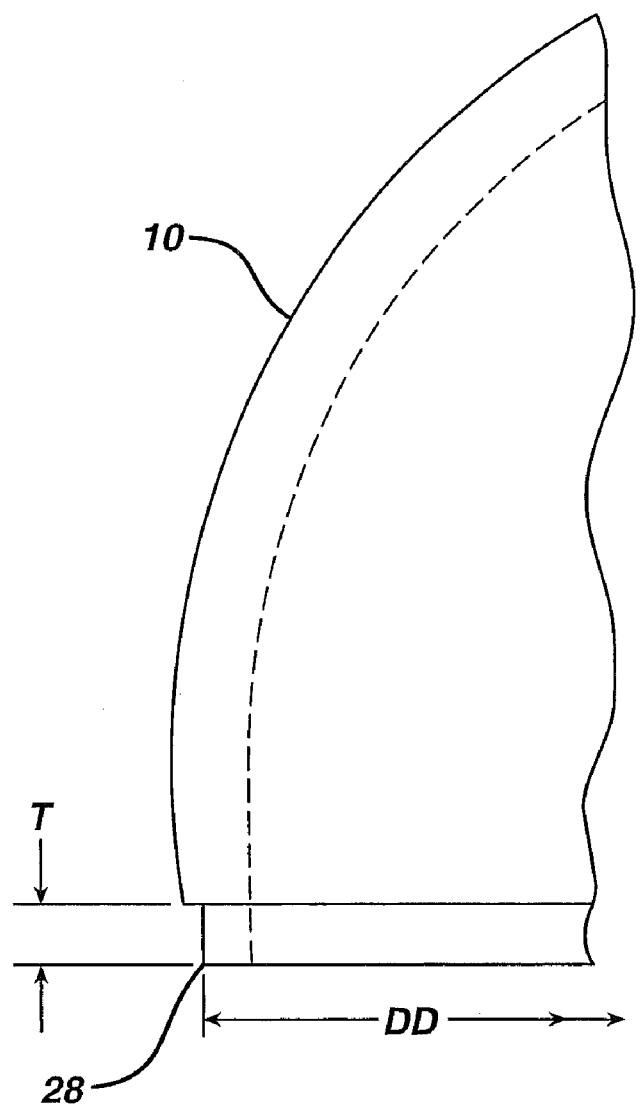
FIG. 2B is a partial plan view of FIG. 2, showing the rim in greater detail.

Referring now to FIG. 2B, the body 14 of the acetabular shell 10 may include a recess or counter bore 38 extending inwardly from the rim 28 of the shell 10. The recess 38 may be defined by a diameter DD and a depth T. The recess 38 may be used in the alignment, insertion and removal of the shell 10.

Figure 3:
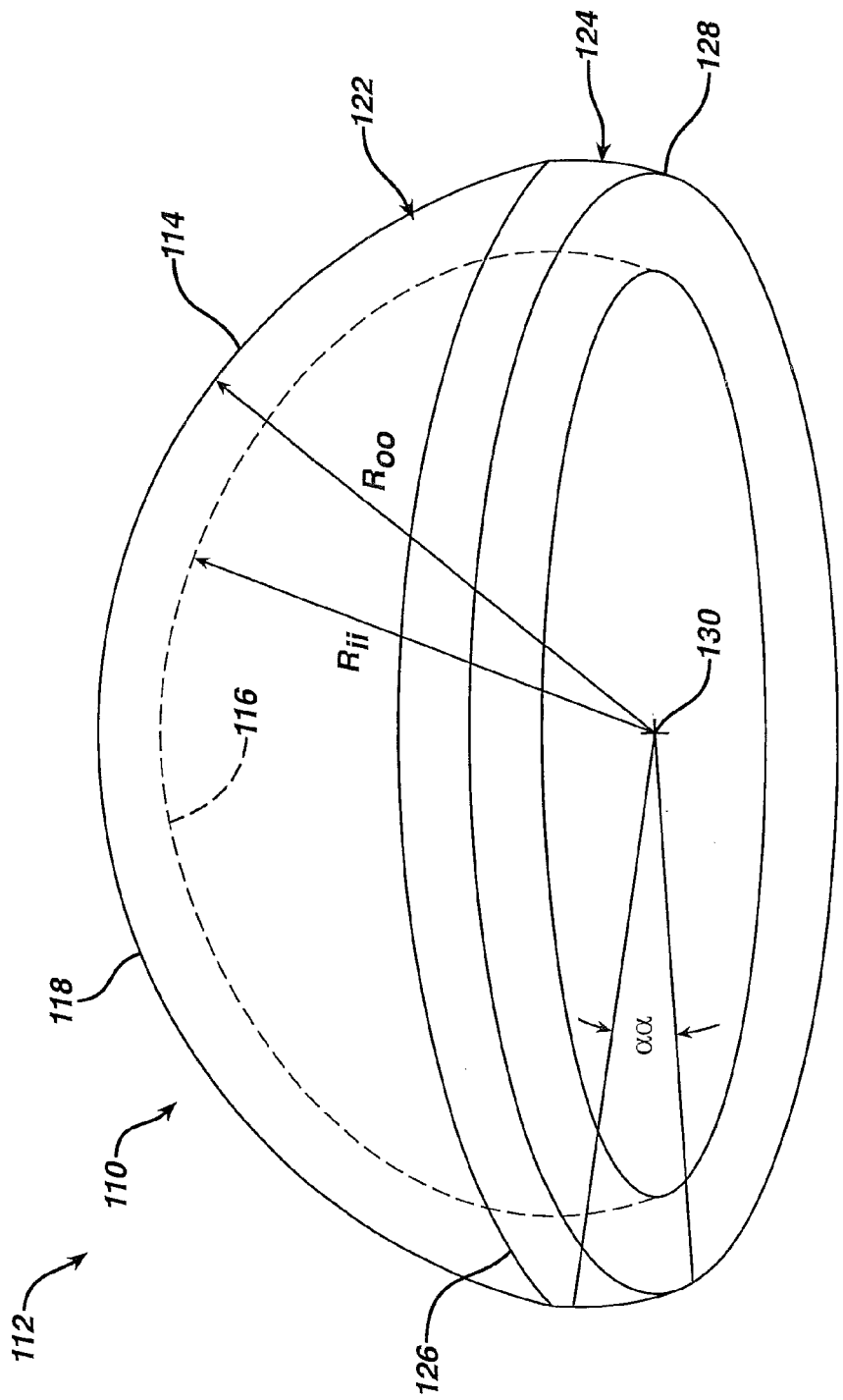
FIG. 3 is a perspective view of an acetabular hip cup in accordance with another embodiment of the present invention without holes for screws.

Referring now to FIG. 3, another embodiment of the present invention is shown as acetabular shell 110. The acetabular shell 110 forms part of hip prosthesis 112. The acetabular shell 110 includes a body 114 having an inner periphery 116 and a convex periphery 118. As shown in FIG. 3 the outer periphery 118 includes a first portion 122 which may be generally hemispherical. The border of the first portion 122 defines an equator 126. The outer periphery 118 further includes a second portion 124 extending from the first portion 122. The second portion 124 extends from equator 126 to rim 128.

As shown in FIG. 3 the inner periphery 116 may be concave and may as shown in FIG. 3 be parallel and spaced from convex outer periphery 118. For example and is shown in FIG. 3, the convex outer periphery 118 may be defined by a locus of points extending a distance Roo from origin 130 while the concave inner portion 116 may be defined by a locus of points extending from radius Rii extending from origin 130. The rim 128 and the equator 126 may define an angle αα extending from origin 130. The angle αα may be any angle capable extending from the equator 126 and may for example from 0 to 20 degrees. The angle αα maybe from 0 to 10 degrees or about 5 degrees.

Figure 4:
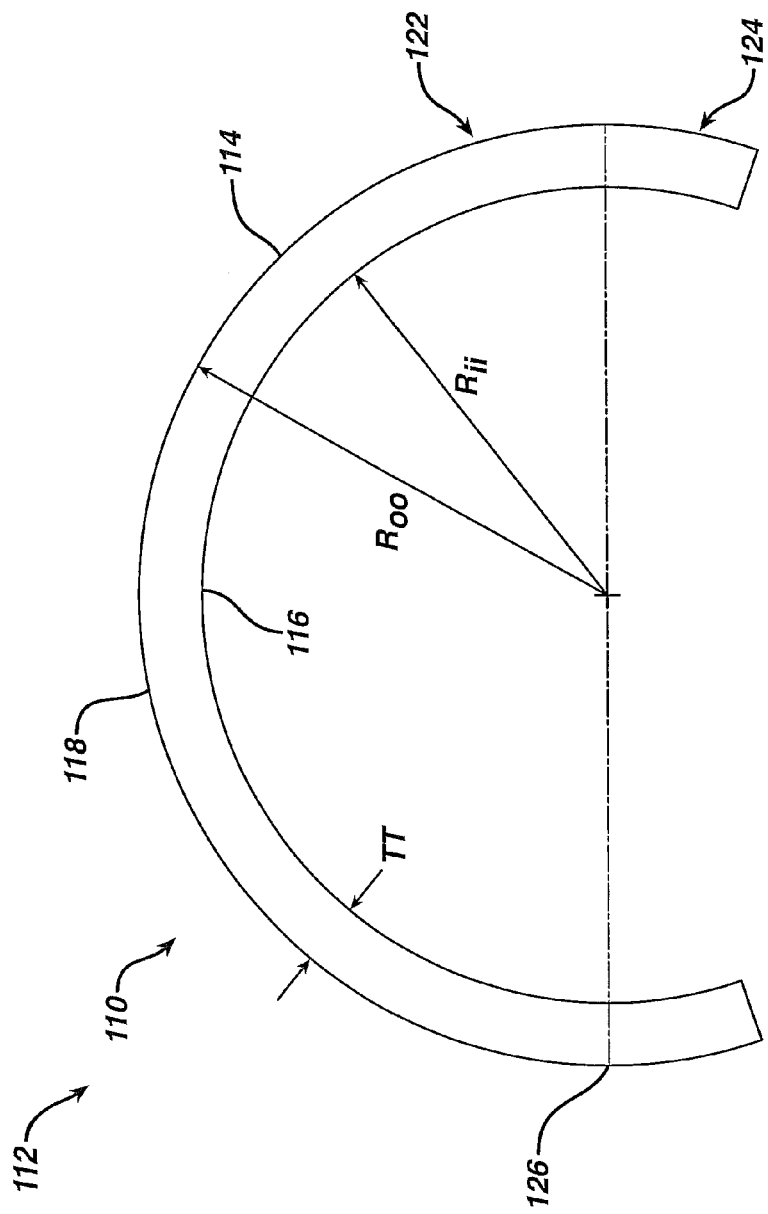
FIG. 4 is cross sectional view of FIG. 3 along the lines 4-4 in the direction of the arrows.

Referring now to FIG. 4, the prosthesis 112 is shown in greater detail. The hip prosthesis 112 may include the acetabular shell 110. The shell 110 may be defined by a body 114 having a convex outer periphery 118 and a concave inner periphery 116. The outer periphery 118 and the inner periphery 116 may both be generally hemispherical and the body 114 may be defined by a thickness TT extending from inner periphery 116 to outer periphery 118. As shown in FIGS. 3 and 4 the acetabular shell 110 may be solid and not include a hole for receiving a fastener in the form of a screw.

Figure 4A:
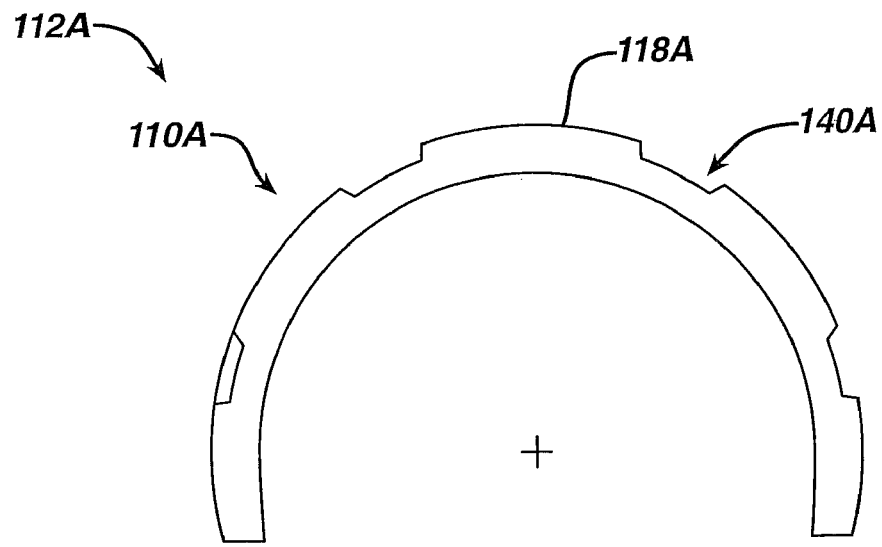
FIG. 4A is a partial plan view of an acetabular hip cup in accordance with yet another embodiment of the present invention with an external periphery with relief areas.

Referring now to FIG. 4A, another embodiment of the present invention is shown as acetabular shell 110A. The acetabular shell 110A is part of the prosthesis 112A. The acetabular shell 110A is somewhat different than the acetabular shell 110 of FIGS. 3 and 4 in that the acetabular shell of 110A includes an outer periphery 118A defining a recess 140A. The recess 140A may be a solitary recess or as shown in FIG. 4A may include a plurality of spaced part recesses 140A. Recesses 140A serve to reduce the surface area of outer periphery 118A.

Figure 4B:
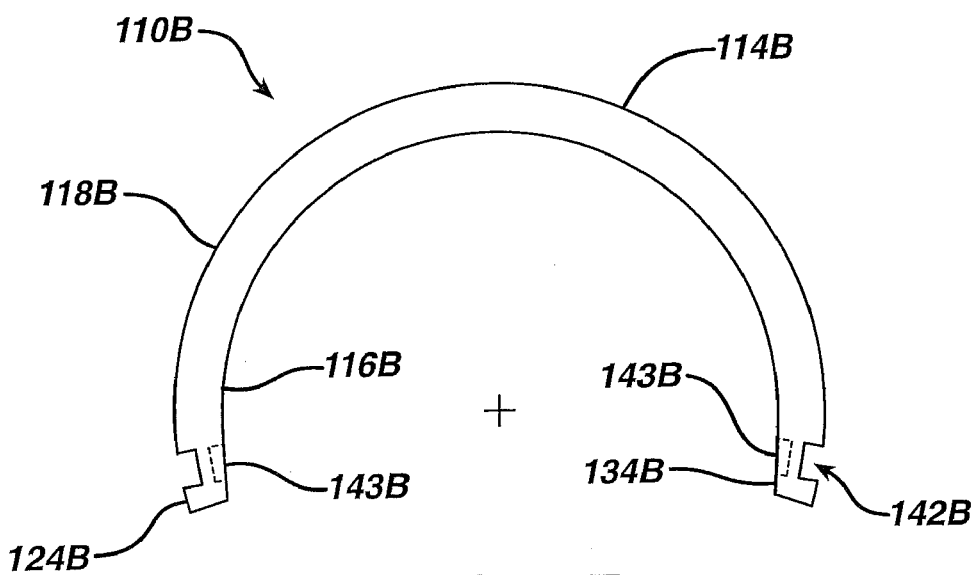
FIG. 4B is a partial plan view of an acetabular hip cup in accordance with yet another embodiment of the present invention with a groove on the external periphery.

Referring now to FIG. 4B, another embodiment of the present invention is shown as acetabular shell 110B. Acetabular shell 110B is similar to acetabular shell 110 of FIGS. 3 and 4 except that the acetabular shell 112B includes a groove 142B positioned on second portion 124B of the convex outer periphery 118B of the body 114B of the acetabular shell 110B. The groove 142B serves to provide a feature for assisting in the removal of the acetabular shell 110B from the acetabulum 5. The groove 142B may also be used for the insertion and the alignment of the acetabular shell 110B within the acetabulum 5. It should be appreciated that a groove 143B may in the alternative or in addition be positioned in the second portion 134B of the inner periphery 116B of the body 114. If positioned in the inner periphery 116B the groove 143B may be utilized to secure a shell, a liner, or bearing insert to the shell 110B.

Figure 4C:
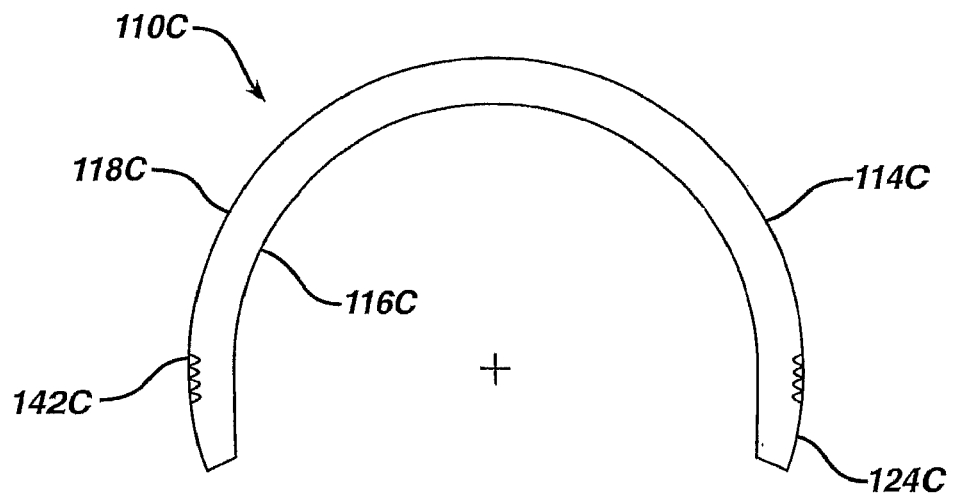
FIG. 4C is a partial plan view of an acetabular hip cup in accordance with yet another embodiment of the present invention with threads on the external periphery.

Referring now to FIG. 4C, another embodiment of the present invention is shown as acetabular shell 110C. The acetabular shell 110C is similar to the acetabular shell 110 of FIGS. 3 and 4 except that the acetabular shell 100C further includes a feature 142C in the form of, for example, external threads. The external threads 142C are positioned in the second portion 124C of the outer periphery 118C of the body 114C of the shell 110C. Threads 142C serve to assist in the removal of the shell 110C from the acetabulum or for the insertion of the shell 110C or for the positioning of the shell 110 within the acetabulum 5. External threads (not shown) may be in the alternative positioned within the inner periphery 116 of the shell 110C.

Figure 4D:
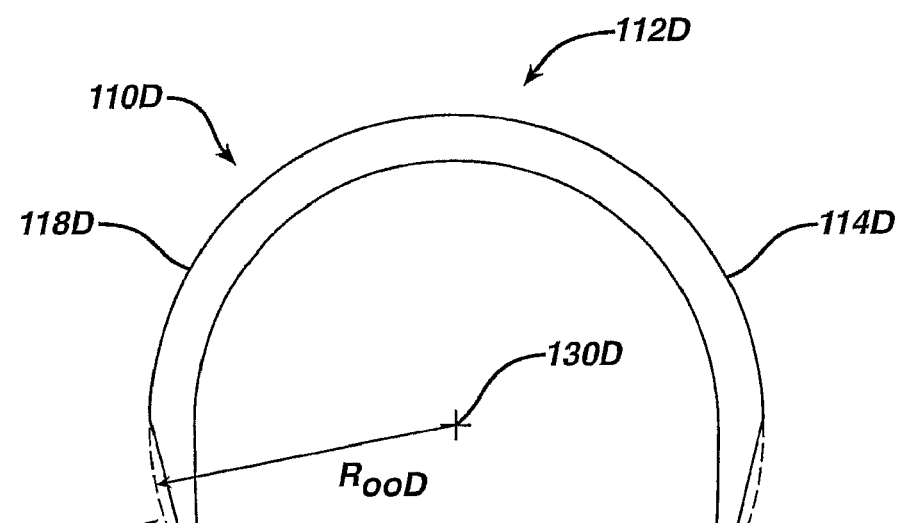
FIG. 4D is a partial plan view of an acetabular hip cup in accordance with yet another embodiment of the present invention with a tapered portion on the external periphery.

Referring now to FIG. 4D, another embodiment of the present invention is shown as hip prosthesis 112D. The hip prosthesis 112D includes an acetabular shell 110D. The acetabular shell 110D is similar to the acetabular shell 110 of FIGS. 3 and 4 except that the acetabular shell 110D includes a body 114D having outer periphery 118D which is somewhat different than the outer periphery 118 of the shell 110 of FIGS. 3 and 4.

For example and is shown in FIG. 4D, the outer periphery 118D of the shell 110D includes a second portion 124D which is tapered inwardly. The second portion 124D is generally conifrustical and as shown in FIG. 4 is positioned inwardly from the locus of points defined by a radius Rood extending outwardly from origin 130D of the shell 110D as shown in phantom.

Figure 6:
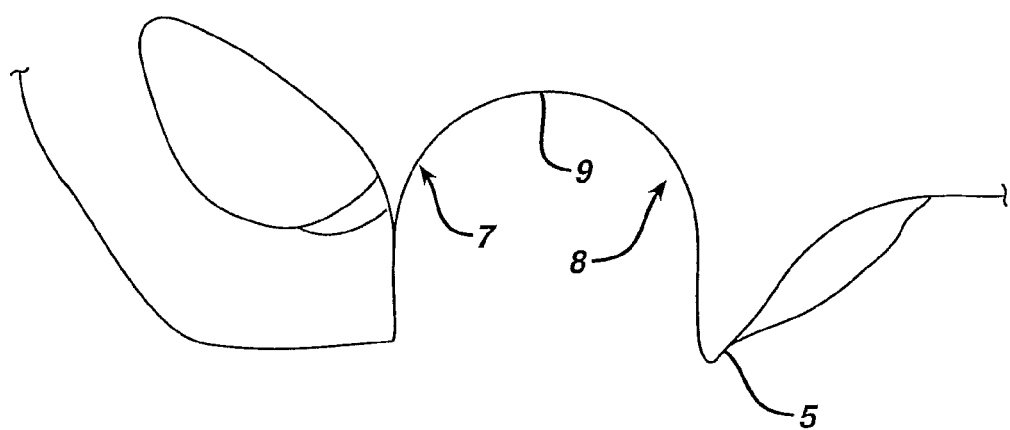
FIG. 6 is a plan view partially in cross section of the acetabulum of a patient prepared for receiving a prosthesis in accordance with the present invention.

Referring now to FIG. 6, the acetabulum 5 is shown in greater detail. The acetabulum 5 includes a pocket 8 having a concave inner periphery 9 defining a seat 7. The seat 7 may be prepared for receiving an acetabular shell by any suitable method. For example, the seat 7 may be prepared by rotating an acetabular reamer within the pocket 8. Such an acetabular reamer, may be, for example, a grater type reamer such as that available from Othy, Inc., Warsaw, Ind.

Figure 7:
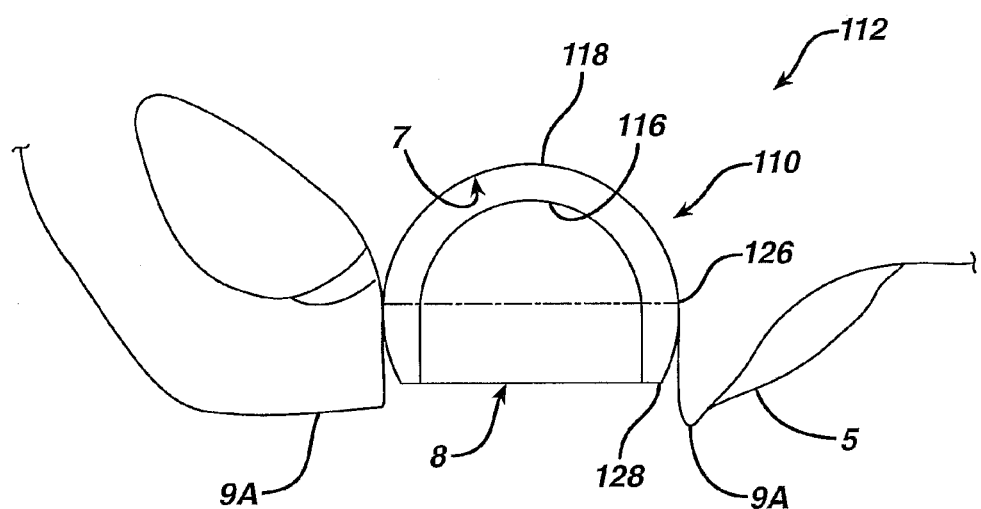
FIG. 7 is a plan view partially in cross section of the hip cup of FIG. 1 shown in position in the acetabulum of a patient.

Referring now to FIG. 7, the acetabular shell 110 of the hip prosthesis 112 is shown in position in the prepared pocket 8 of the acetabulum 5. The convex outer periphery 118 of the acetabular shell 110 is fitted against the seat 7 of the pocket 8 of the acetabulum 5. As can be seen in FIG. 7, the rim 128 of the acetabular shell 110 is preferably positioned within or inside the outer portions 9A of the acetabulum 5.

Figure 8:
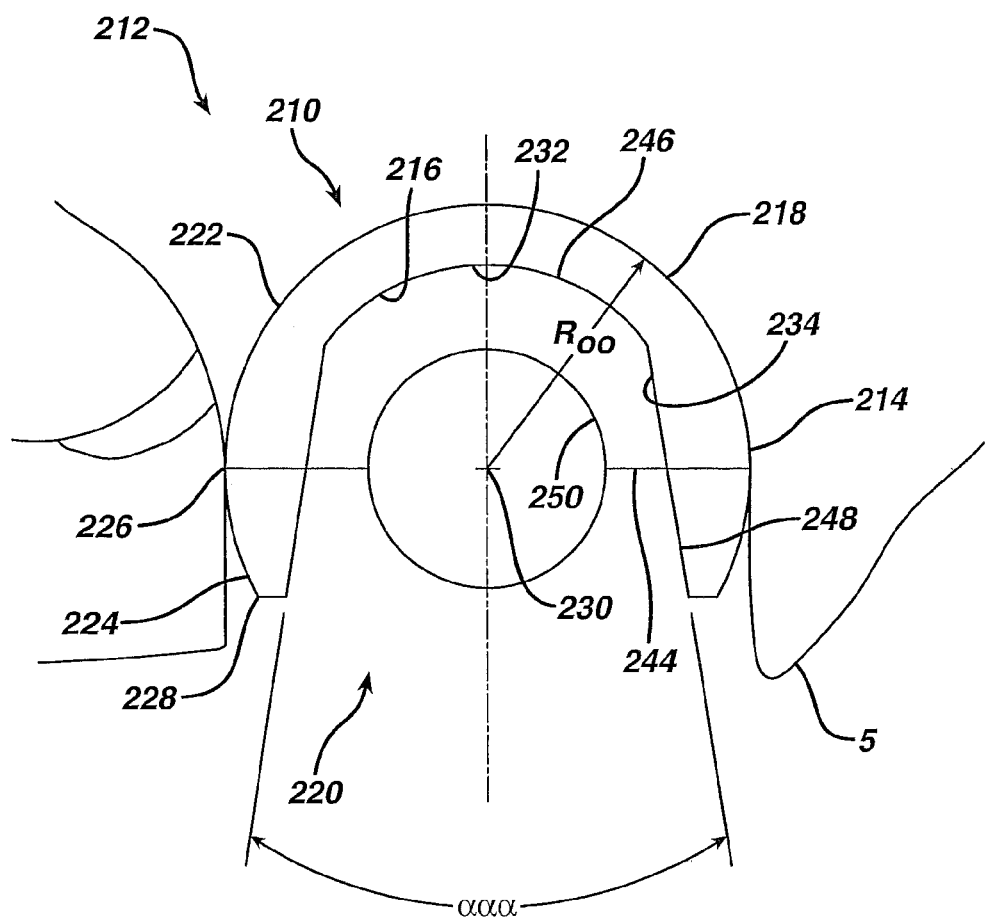
FIG. 8 is an enlarged plan view partially in cross section of an acetabular hip cup in accordance with yet another embodiment of the present invention with a tapered portion as shown in position in the acetabulum of a patient.

Referring now to FIG. 8, another embodiment of the present invention is shown as hip prosthesis 212. The hip prosthesis 212 includes an acetabular shell 210 defining a cavity 220 therein. The hip prosthesis 212 further includes a bearing or liner 244 positioned in the cavity 220 of the shell 210.

The acetabular shell 210 may be somewhat similar to the acetabular shell 110 of FIGS. 3 and 4. The acetabular shell 210 includes a body 214 having a convex outer periphery 218 and a spaced-apart inner periphery 216. The convex outer periphery 218 includes a generally hemispherical first portion 222 defining an equator 226.

The convex outer periphery 218 further includes a second portion 224 extending from the equator 226 to rim 228. The first portion 222 and the second portion 224 may be defined for example, by a locus of points extending from radius Roo to origin 230. The inner periphery 216 of the acetabular shell 210 is somewhat different than the inner periphery 110 of the shell of FIGS. 3 and 4.

For example, and is shown in FIG. 8 the inner periphery 216 includes first portion 232 having generally hemispherical shape. The inner periphery 216 may further include a second portion 234 extending outwardly from the first portion 232. The second portion 234 has a generally tapered shape or is generally conifrustical. The second or tapered portion 234 defines an included angle ααα of for example about 0 to 20 degrees. Preferably the angle ααα is selected to provide for a self-locking taper of the liner 244 to the acetabular shell 210.

To provide for a self-locking taper the angle ααα may be determined by maintaining the formula:

$$\tan(\alpha\alpha\alpha/2) \leq \mu$$

where: ααα=the included angle of the taper
μ=coefficient of friction of the surface of the taper The liner 244 includes a periphery 246 including a conifrustical portion 248. The conifrustical portion 248 is designed to matingly fit with tapered portion 234 of the shell 110. The liner 244 further includes a generally hemispherical inner portion 250. The hemispherical portion 250 is designed to mate with for example, the head or ball of the prosthesis.

The liner 244 may be made of any suitable, durable material and may for example, be made of a metal, a ceramic, or a plastic. If made of a metal, the liner 244 may be made of, for example, a cobalt chromium alloy, a titanium alloy, or a stainless steel alloy. If made of a plastic, the liner 244 may be made of highly cross-linked ultra high molecular weight polyethylene.

Figure 9:
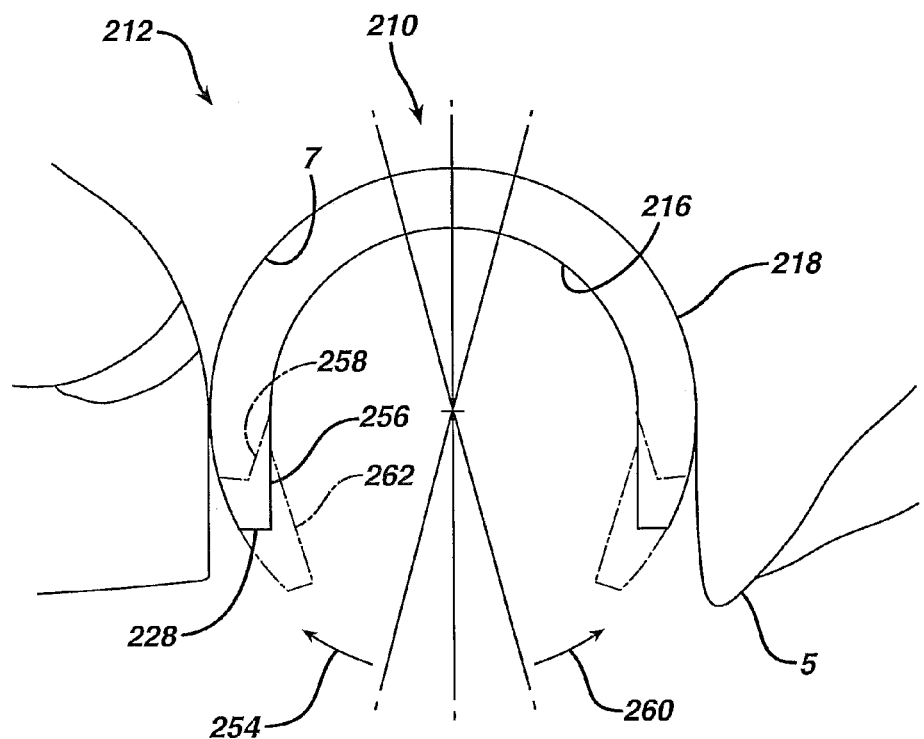
FIG. 9 is an enlarged plan view partially in cross section of the hip cup of FIG. 8 shown rotated in various positions in the acetabulum of a patient.

Referring now to FIG. 9, the acetabular shell 210 of the hip prosthesis 212 is shown in position on the acetabulum 5. As shown in FIG. 9, the shell 210 may be rotated with respect to of the acetabulum 5. For example and is shown FIG. 9, acetabular shell 210 may be rotated in a first direction 254 such that the shell moves from first position 256 as shown as solid to second position 258 as shown in dash lines. Alternatively, the acetabular shell may be rotated in the direction of the arrow 260 from first position 256 as shown in solid to third position 262 as shown in phantom. It should be appreciated that the prosthesis 212 may be utilized to position the acetabular shell 210 to the seat 7 in order to optimize the range of motion for the patient depending on the physical characteristics of the patient and potential impingement to the acetabulum 5.

Figure 10:
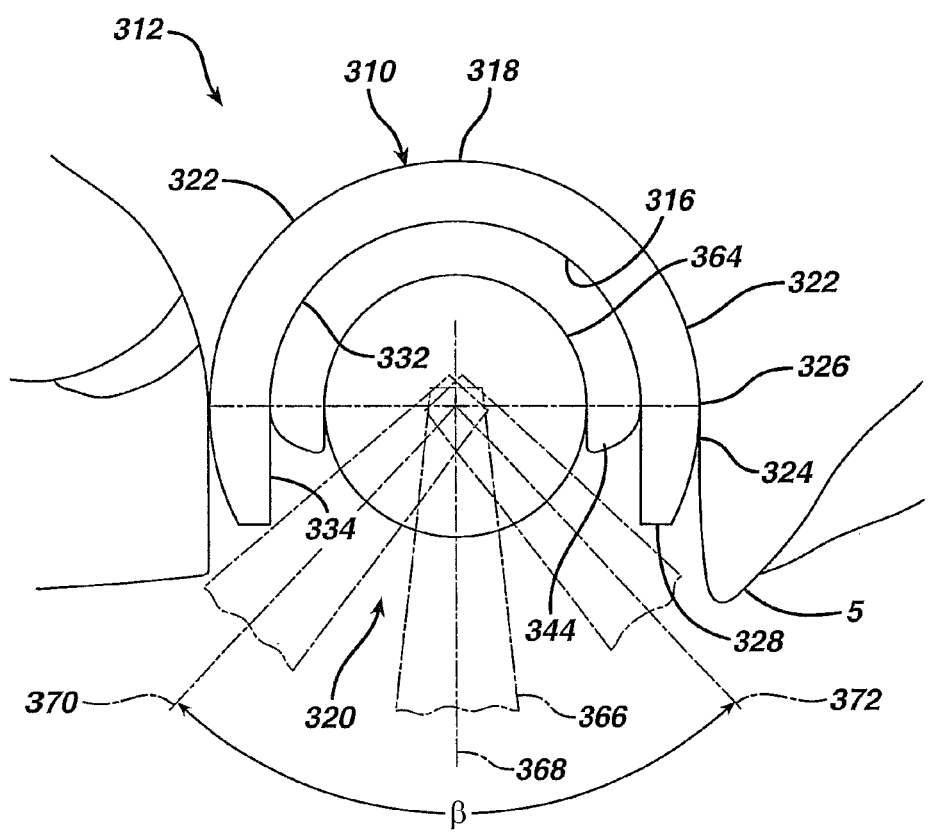
FIG. 10 is an enlarged plan view partially in cross section of an acetabular hip cup in accordance with yet another embodiment of the present invention with a deep unrestrained liner positioned in the cup.

Referring now to FIG. 10, another embodiment of the present invention is shown as hip prosthesis 312. The prosthesis 310 includes an acetabular shell 310, which defines a cavity 320 therein. Positioned in the cavity 320 is a liner 344. The acetabular shell 310 includes an outer periphery 318 including a first portion 322 which is generally hemispherical, and bounded by an equator 326. The shell 310 also includes a second portion 324 extending from equator 326 to rim 328.

The acetabular shell 310 further includes an inner periphery 316 having a first portion 332 which is generally hemispherical, and a second portion 334 extending from the first portion 332. The second portion 334 may, as shown in FIG. 10, may be generally cylindrical. The liner 344 may be fitted within the cavity 320 of the acetabular shell 310. The hip prosthesis 312 may further include a head 364 mattingly fitted to the liner 344 and a stem 366 operably connected to head 364. The stem 366 may be fitted to for example, the medullary canal of a long bone (not shown).

Stem 366 may define a longitudinal axis 368 of the stem 366. The permitted motion of the centerline 368 of the stem 366 may be defined an angle β from first portion 370 to second position 372. The angle β may define the range of motion in the patient. It should be appreciated that based on the positioning of the acetabular shell 310 within the acetabular 5, the angle β and the resulting range of motion may be limited by impingement on the acetabulum 5, the acetabular shell 310, or the liner 344.

Figure 11:
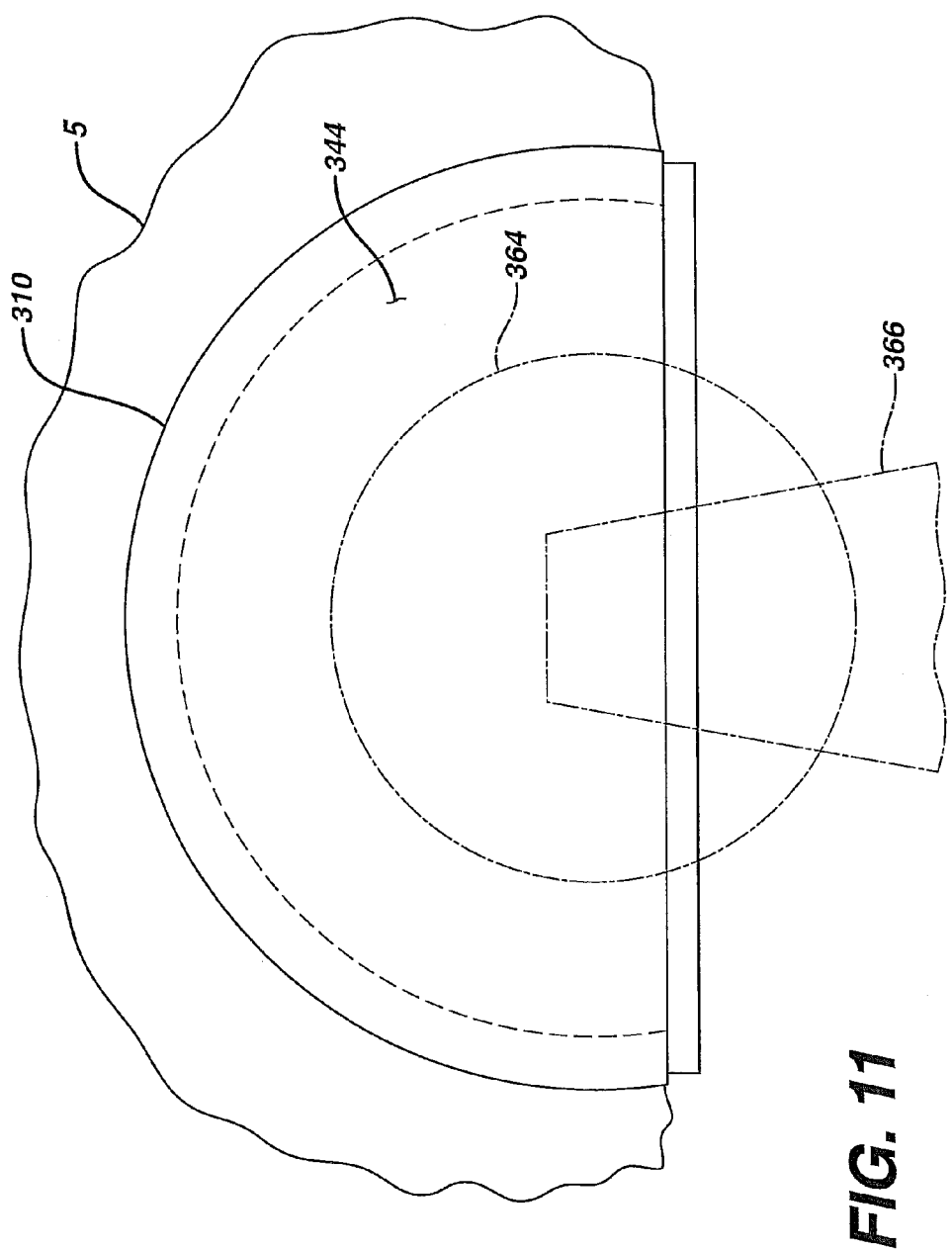
FIG. 11 is plan view of the hip cup of FIG. 10.

Referring now to FIG. 11, the acetabular shell 310 is shown in position in acetabulum 5. The liner 344 is positioned within the shell 310 and the head or ball 364 is positioned within the liner 344. The stem 366 is connected to the head 364.

Figure 12:
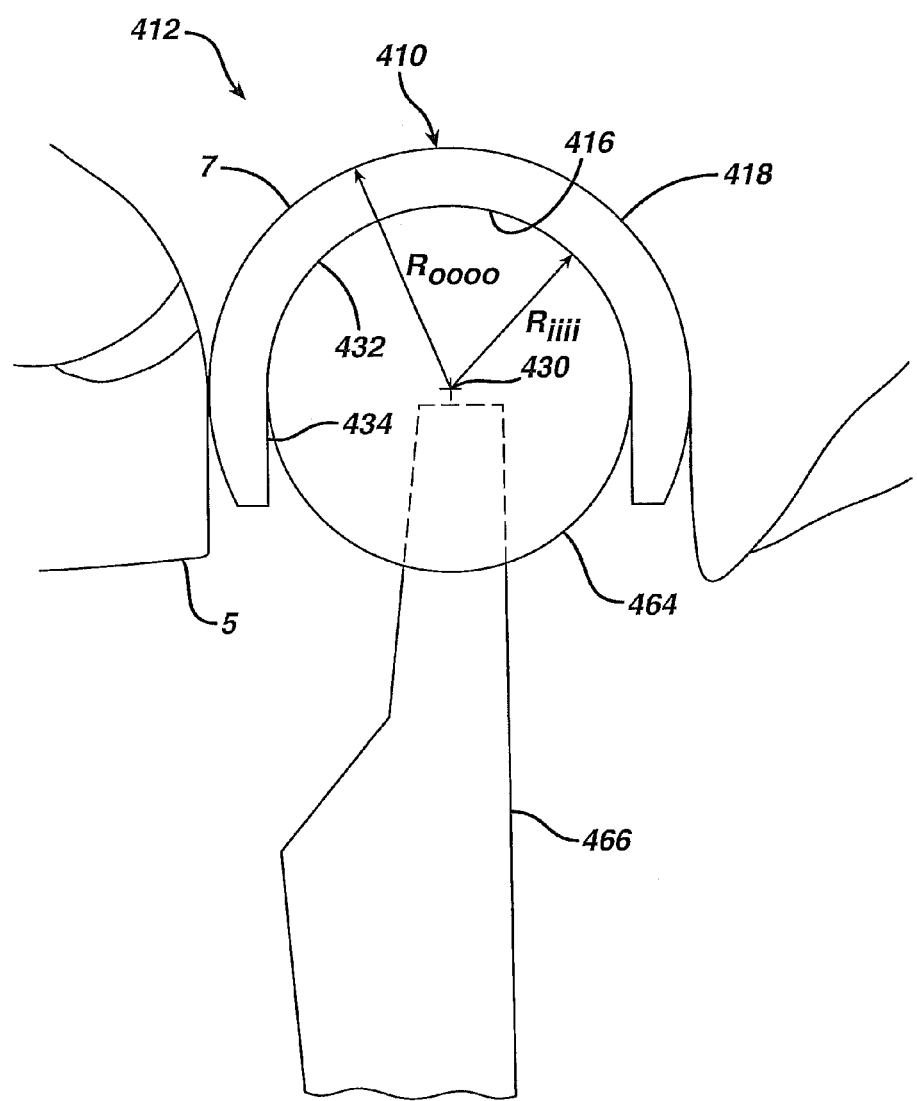
FIG. 12 is an enlarged plan view partially in cross section of an acetabular hip cup in accordance with yet another embodiment of the present invention with no liner and a head positioned in the cup.

Referring now to FIG. 12, another embodiment of the present invention is shown as hip prosthesis 412. The prosthesis 412 includes an acetabular shell 410. The acetabular shell 410 mattingly fits to seat 7 of the acetabulum 5. The shell 410 includes an outer periphery 418 that is convex. The convex outer periphery 418 includes a periphery that is defined by a locus of points extending a distance Roooo from origin 430. The shell 410 further includes an inner periphery 416. The inner periphery 416 includes a hemispherical portion 432 defined by a radius Riii extending from origin 430. The inner periphery 416 further includes a second portion 434 extending from the first portion 432 and having a generally cylindrical shape defined by radius Riii. Unlike the hip prosthesis 312 of FIGS. 10 and 11, the hip prosthesis 412 does not include a liner and the head 464 of the hip prosthesis 412 matingly rotates in the inner periphery 316 of the shell 410. A stem 466 may be attached to the head 464. The stem 466 may be further secured in a canal of a long bone (not shown).

Figure 13:
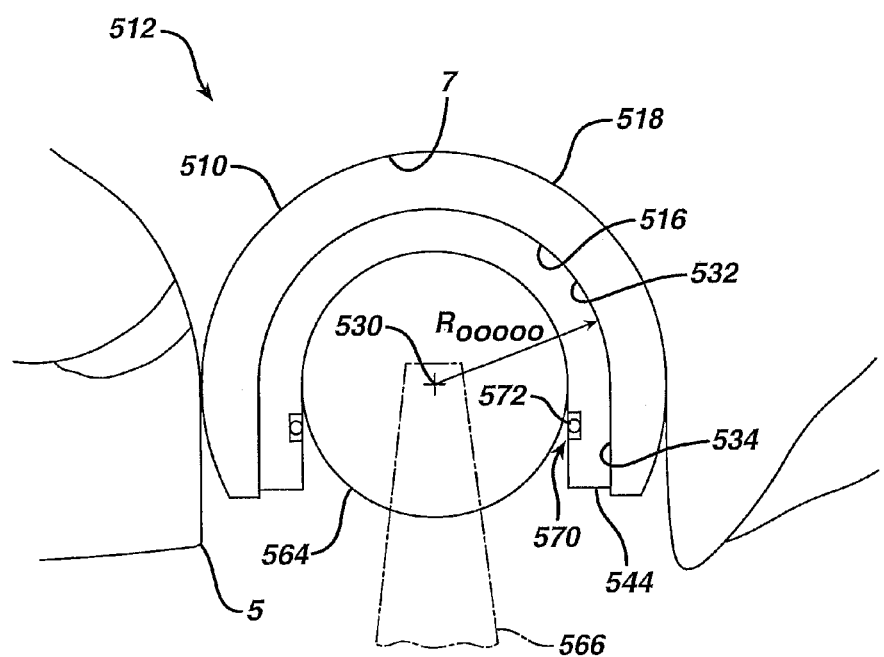
FIG. 13 is an enlarged plan view partially in cross section of an acetabular hip cup in accordance with yet another embodiment of the present invention with a deep restrained liner positioned in the cup and a head positioned in the liner.

Referring now to FIG. 13 another alternate embodiment of the present invention is shown as hip prosthesis 512. The hip prosthesis 512 includes an acetabular shell 510 which matingly fits to the seat 7 of the acetabulum 5. The shell 510 includes a convex outer periphery 518. The convex outer periphery 518 is defined by locus of points extending distance Rooooo from origin 530. The shell 510 is further defined by an inner periphery 516. The inner periphery includes a first concave portion 532, which is generally hemispherical. Extending from the first portion 532 is a second portion 534. The second portion 534 is generally cylindrical.

The hip prosthesis 512 further includes a liner or bearing 544. The liner 544 is somewhat different from the liner 344 of FIGS. 10 and 11 in that the liner 544 includes a constraining feature 570 in the form of, for example, a groove which mates with, for example, an o-ring or retainer 572. The retainer 572 serves to restrain the head 564 within the liner 544. A stem 566 extends outwardly from the head 564 and may be fitted within the medullary canal of a long bone (not shown). The retainer 510 maybe in cooperation with the head 564 and the liner 544 to secure or retain the head 564 within the liner 544 to inhibit hip prosthesis separation or disengagement.

Figure 14:
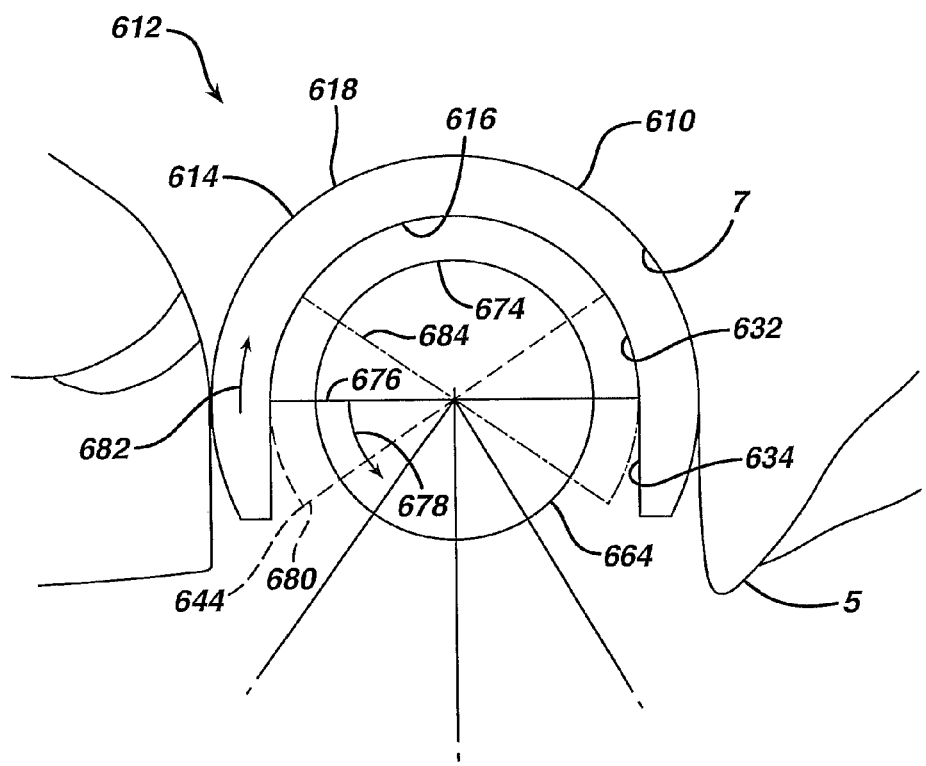
FIG. 14 is an enlarged plan view partially in cross section of an acetabular hip cup in accordance with yet another embodiment of the present invention with a hemispherical unrestrained liner shown rotated in various positions in the hip cup.

Referring now to FIG. 14, another embodiment of the present invention is shown as hip prosthesis 612. The hip prosthesis 612 may include a shell 610, which matingly fits to seat 7 of the acetabulum 5. The acetabular shell 610 includes a body 614 having a convex outer periphery 618 and an inner periphery 616. The inner periphery 616 may include a first portion 632, which is generally hemispherical, and a second portion 634 extending from the first portion 632. The second portion 634 may be generally cylindrical. A liner 644 may be fittingly positioned to the inner periphery 616 of the shell 610. The liner 644 may include an inner periphery 674 which is generally concave and hemispherical and which is matingly fitted to head 664. The liner 644 as shown in. FIG. 14 may be movably positioned relatively to the inner periphery 616 of the shell 610. For example and as shown in FIG. 14, the liner 644 may be moved from first position 676 as shown in solid in the direction of arrow 678 to second position 680 as shown in dashed lines. Similarly, the liner 644 may be moved from first position 676 in the direction of arrow 682 to third position 684 as shown in phantom.

The permitted motion of the liner 644 within the shell 610 provides for increased range of motion to the hip prosthesis 612. Such increased motion is available by eliminating the limitation of the movement of the hip prosthesis 612 caused by impingement of the liner 644 against the stem (not shown) of the hip prosthesis 612.

It should be appreciated that a restraining mechanism (not shown) may be positioned in the shell 610 between the liner 644 and the shell 610 to prevent the liner 644 from being separated from the shell 610. Further it should be appreciated that the liner 644 may further include a restraining mechanism (not shown) to restrain the liner 644 to stay in its position in the shell 610. The liner 644 may also may also include a restraining mechanism (not shown) to restrain head 664 within the liner 644.

Figure 15:
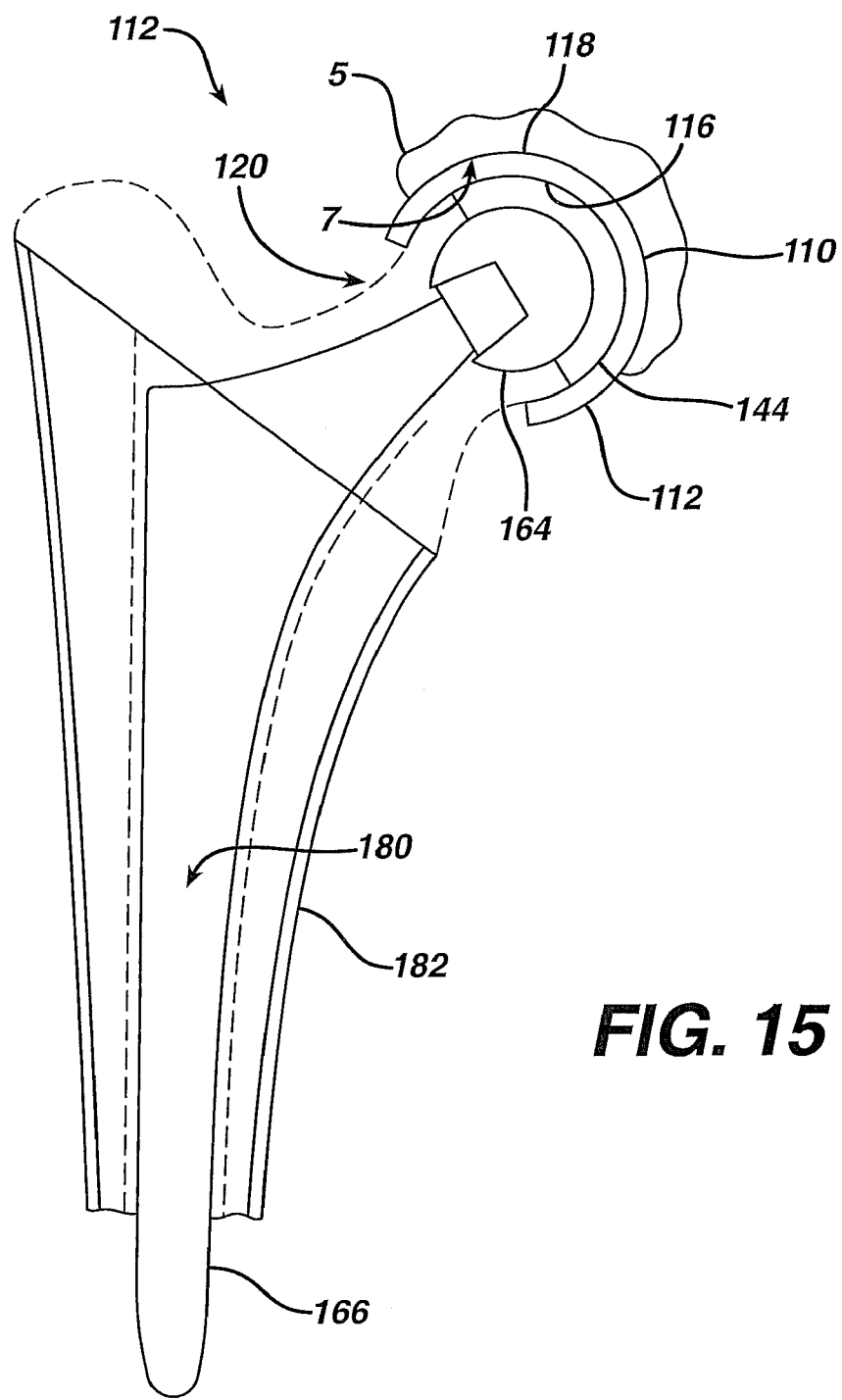
FIG. 15 is a plan view partially in cross section of a hip prostheses including a femoral stem and the hip cup of FIG. 1.

Referring now to FIG. 15, shell 110 is shown as a part of hip prosthesis 112. The hip prosthesis 112 includes in additional to the shell 110 a liner 144, which fits into the cavity 120 formed within the shell 110. A head 164 may be matingly fitted to the liner 144. The stem 166 may be fitted to the head 164. The stem 166 may fit within the medullary canal 180 of femur 182.

Referring now to FIG. 16, a method for performing arthoplasty according to the present invention is shown as method 700. The method 700 includes the first step 702 of providing a hip prosthesis including a shell. The shell has an external spherical periphery extending beyond the equator of the spherical periphery. The method includes a second step 704 in cutting an incision into the patient. The method 700 further includes a third step 706 of preparing the acetabulum for receiving the shell. The method further includes a fourth step 708 of assembling the shell into the acetabulum, as well as, a fifth step 710 of orienting the shell relative to the acetabulum to optimize the prosthesis.

Although the present invention and its advantages have been described in detail, it should be understood that various changes, substitutions, and alterations can be made therein without departing from the spirit and scope of the present invention as defined by the appended claims.

We claim:

1. A hip cup for use in hip prosthesis, said cup comprising:
a shell comprising a body having a first portion and a second portion, the first portion having an inner periphery and an outer periphery, the outer periphery defining a hemisphere and having a first radius, the second portion has an inner periphery and an outer periphery, the outer periphery of the second portion extending from the equator of the first portion in a converging direction and creating a rim, the outer periphery of the second portion having a second radius that is equal to the first radius, wherein the inner periphery of the first portion is hemispherical and the inner periphery of the second portion extends from the equator of the inner periphery of the first portion and the inner peripheries of the first and second portion define a cavity, wherein the entire inner periphery of the second portion is defined by an internal wall which defines an opening into the cavity, and the entire internal wall is cylindrical or flared outwardly toward the rim of the second portion; and
a liner to cooperate with the shell.

2. The acetabular shell of claim 1, wherein the inner periphery of the first portion is substantially concave.

3. The acetabular shell of claim 1, wherein the inner periphery of the first portion is substantially concentric with the outer periphery.

4. The acetabular shell of claim 1, wherein at least one of the outer periphery of the first portion and the second portion of said body is defined by a locus of points extending a fixed distance from an origin.

5. The acetabular shell of claim 1, wherein the outer periphery of both the first portion and the second portion of said body is defined by a locus of points extending a fixed distance from an origin.

6. The acetabular shell of claim 1, wherein the rim is spaced from and generally parallel to the equator.

7. The acetabular shell of claim 6, wherein the rim and the equator define an angle extending from the origin.

8. The acetabular shell of claim 7, wherein the angle is from 0 to 20 degrees.

9. The acetabular shell of claim 8, wherein the angle is from 0 to 10 degrees.

10. The acetabular shell of claim 9, wherein the angle is from 5 to 8 degrees.

11. A hip prosthesis for use in hip arthroplasty, said prosthesis comprising:
a stem for implantation into the medullary canal; and
a hip cup including a liner and a shell, the shell having a body having a first portion and a second portion, the first portion having an inner periphery and an outer periphery, the outer periphery defining a hemisphere and having a first radius, the second portion has an inner periphery and an outer periphery, the outer periphery of the second portion extending from the equator of the first portion in a converging direction and creating a rim, the outer periphery of the second portion having a second radius that is equal to the first radius, wherein the inner periphery of the first portion is hemispherical and the inner periphery of the second portion extends from the equator of the inner periphery of the first portion and the inner peripheries of the first and second portion define a cavity, wherein the entire inner periphery of the second portion is defined by an internal wall which defines an opening into the cavity which, in its entirety, is cylindrical or flared outwardly toward the rim of the second portion.

12. The hip prosthesis of claim 11, wherein at least one of the first portion and the second portion of the outer periphery of said body is defined by a locus of points extending a fixed distance from an origin.

13. The hip prosthesis of claim 12, wherein the first portion and the second portion of the outer periphery of said body is defined by a locus of points extending a fixed distance from an origin.

14. The hip prosthesis of claim 13, wherein the rim is spaced from and generally parallel to the equator.

15. The hip prosthesis of claim 14, wherein the rim and the equator define an angle extending from the origin.

16. The hip prosthesis of claim 15, wherein the angle is from 0 to 10 degrees.

17. The hip prosthesis of claim 16, wherein the angle is from 0 to 5 degrees.

\* \* \* \* \*